United States Patent [19]

Stiefel

[11] 4,310,674

[45] Jan. 12, 1982

[54] OXAZOLIDINE PROPIONIC ACID METHYL ESTERS

[75] Inventor: Frank J. Stiefel, Princeton, N.J.

[73] Assignee: Carter-Wallace, Inc., New York, N.Y.

[21] Appl. No.: 170,027

[22] Filed: Jul. 18, 1980

[51] Int. Cl.³ .................. C07D 263/04; A61K 31/42
[52] U.S. Cl. ..................................... 548/215; 424/272
[58] Field of Search ......................................... 548/215

[56] References Cited
U.S. PATENT DOCUMENTS

| | | | |
|---|---|---|---|
| 1,972,465 | 9/1934 | Ulrich et al. | 548/215 |
| 3,974,173 | 8/1976 | Kelly | 548/215 |
| 4,116,970 | 9/1978 | Ochsner | 548/215 |

*Primary Examiner*—Anton H. Sutto
*Attorney, Agent, or Firm*—Kevin B. Clarke

[57] ABSTRACT

A novel chemical compounds of the formula

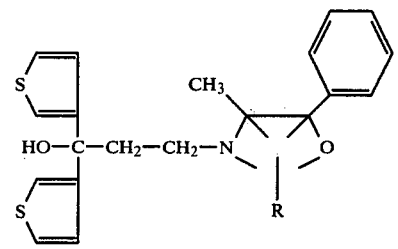

wherein R is hydrogen or branched or straight chain lower alkyl of from 1–6 carbon atoms as well as methods for preparing such compounds.

6 Claims, No Drawings

OXAZOLIDINE PROPIONIC ACID METHYL ESTERS

This invention relates to a novel precursor of 1-(+)-α-[1-(3,3-di-3-thienyl-2-propenyl) amino ethyl] benzenemethanol hydrochloride and methods for preparing such precursor.

Basic dithienyl compounds are well known pharmacologically active compounds which are useful in the treatment of heart and circulatory illnesses. The compounds cause a widening of the coronary vessels and thereby increase the peripheral and cerebral blood flow. This effect is accompanied in a number of cases by a positive inotropic effect. The basic dithienyl compounds are useful in other areas such as curing agents in addition to the human and veterinary medicine fields.

The basic dithienyl compound of the present invention has been previously prepared in accordance with the procedures set out in U.S. Pat. No. 3,766,173 wherein compounds of the formula:

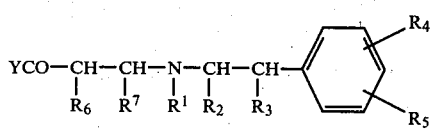

Where Y is chlorine, bromine and alkoxy group or a thienyl group and $R_1$, $R_2$, $R_6$ and $R_7$ are the same or different and are hydrogen or lower alkyl, $R_3$ is hydrogen or hydroxyl and $R_4$ and $R_5$ are the same or different and are hydrogen, halogen, hydroxyalkyl, lower alkyl, lower haloalkyl or lower alkoxy and their pharmacuetically acceptable salts are reacted with thienyl metal compounds and are converted to the corresponding unsaturated compounds and subsequently converted by known methods to the salts.

The process for the reaction of the ketone with a thienyl metal compound is suitably carried out at a temperature between −70° C. and +100° C. While in the preparation of many of the compounds a lower limit of −40° C. is sufficient when the reaction involves a thienyl-(3)-metal compound the reaction goes most smoothly below −40° C., for example −70° C. As the reaction medium an organic solvent such as dialkyl ethers, e.g. diethylether tetrahydrofuran, hydrocarbons, benzene, etc. can be used. When Y in the formula is a thienyl group only one mole of thienyl metal compound is necessary for the reaction while two moles of thienyl compound are necessary if Y is chlorine, bromine or an alkoxy group. As thienyl metal compounds thienyl lithium and thienyl gingnard compounds, e.g. thienyl magnesium chloride and thienyl magnesium bromide are of primary importance.

However, The procedure outlined in U.S. Pat. No. 3,766,173 always requires an excess of metallo organic compound when active hydrogen is present in the reactant.

Moreover, the overall yield of basic dithienyl compound produced via the prior art processes is on the order of about 11%.

I have now found that the overall yield of basic dithienyl compound can be more than doubled to a yield of on the order of 50% and higher using a novel cyclic intermediate compound.

In accordance with the present invention, the basic dithienyl compound:

1-(+)-α-[1-(3,3-di-3-thienyl-2-propenyl) amino ethyl] benzenemethanol hydrochloride is produced when the new compounds of the formula:

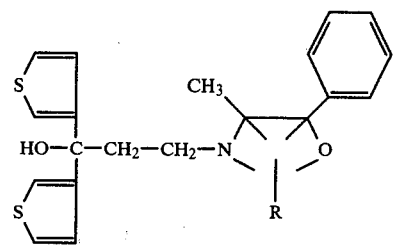

wherein R is hydrogen, lower alkyl or branched chain lower alkyl of from 1-6 carbon atoms is subjected to hydrolysis.

The precursor of the novel intermediate compounds of the present invention is an oxazolidine propionic acid alkyl ester which is obtained by reacting an alkyl acrylate and l-norphedrine in an appropriate organic solvent such as toluene, THF, alcohols, benzene, ethyl ether, hydrocarbons, etc, at ambient temperature and pressure for about 24 hours. Thereafter an aldehyde of the formula

RCHO wherein R is H. lower alkyl of from 1 to 6 carbon atoms or branched chain lower alkyl of from 1 to 6 carbon atoms, is added to the reaction mixture and the mixture is heated to remove the water formed. When no more water can be removed, the solution is concentrated and distilled to obtain the oxazolidine propionic acid methyl ester.

The oxazolidine propionic acid methyl ester is subsequently reacted with two moles of the reaction product of 3-bromo thiophene and n-butyl lithium at reduced temperatures to obtain α, α, (di-3-thienyl)-4-methyl-5-phenyl-2-isopropyl-3-oxazolidine propanol which is recovered and hydrolyzed to 1-(+)-α-[1-(3,3-di-3-thienyl-2-propenyl) amino ethyl] benzenemethanol hydrochloride.

The novel intermediate compounds of the invention as well as the basic thienyl compounds can be conveniently prepared according to the following synthetic route.

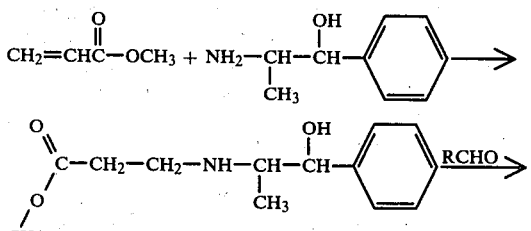

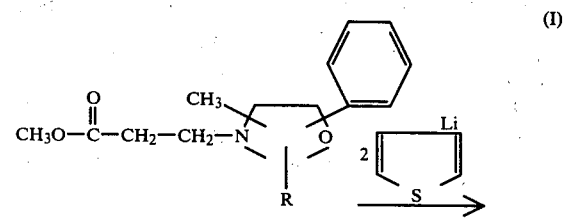

(I)

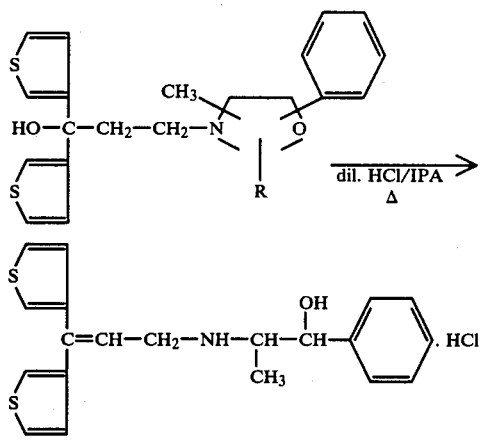

The following examples serve to illustrate the preferred methods of preparation and are given by way of illustration only and in no event are to be construed as limiting.

EXAMPLE 1

4-METHYL-5-PHENYL-2-ISOPROPYL-3-OXAZOLIDINE PROPIONIC ACID METHYLESTER (COMPOUND I)

100 ml. of toluene, 43 g. (0.5 moles) of methyl acrylate and 76 g. (0.5 moles) of l-norephedrine are added to a 500 ml. three neck flask and stirred at room temperature for 24 hours. To the solution is added 50.4 g. (0.7 mole) of isobutyraldehyde and the mixture is heated to remove the water formed, by azeotropic distillation. When no more water can be removed, concentrate and distill. The oxazolidine proprionic acid methylester boils at 140°–160° C./0.5 mm. The yield is 129 g. (87%) $n^{23}{}_d = 1.5020$.

EXAMPLE 2

α,α(di-3-thienyl)-4-METHYL-5-PHENYL-2-ISOPROPYL-3-OXAZOLIDINE PROPANOL (COMPOUND II)

Add 163 g. (1.0 moles) of 3-bromo thiophene in 600 ml. of anhydrous ether to a three liter three neck flask equipped with a stirrer, dropping funnel and dry ice condenser. Sweep the flask with nitrogen and with good stirring, drip in 64 g. (1.0 mole) of n-butyllithium (1.6 M in hexane) while keeping the reaction temperature at −60° to −70° C. with dry ice/acetone bath. Stir an additional one half hour at −70° C. while a solid precipitates. Add 125 g. (0.43 mole) of Compound 1 keeping the temperature −60° to −70° C., and stir for 15 minutes at −70° C. Remove the dry ice bath and continue stirring while the temperature slowly rises to 0° C. (1½ hours). Decompose the reaction mixture by the slow addition of 500 ml. of water, never letting the temperature go above 25° C. Separate the organic layer and wash with 500 ml. of water. Concentrate the organic layer in vacuo on a steam bath to an oil, cool to 50° C. and add 500 ml. of hexane to crystallize. Filter and dry, the yield is 134 g. (73%), M.P. 125°–7° C.

calc. for $C_{24}H_{29}NO_2S_2$: Theory: C=67.45%; H=6.79%; N=3.28%; S=14.99%. Found: C=67.76%; H=6.97%; N=3.17%; S=14.27%

EXAMPLE 3

1-(+)-α-[1-(3,3-di-3-THIENYL-2-PROPENYL) AMINO ETHYL] BENEZENEMETHANOL HYDROCHLORIDE (COMPOUND III)

20 g. of Compound II is refluxed with 100 ml. of isopropanol to dissolve the solid. 30 ml. of 10% aqueous hydrochloric acid is added and the solution heated to remove isobutraldelyde. As the aldehyde is removed a solid precipitates. Continue to heat for ½ hour, add 50 ml. of isopropanol to the mixture and cool in the refrigerator overnight. Filter and obtain 15.8 g. (86%) of Compound III, M.P. 231°–233° C.

The overall yield of Compound III is 56% based on l-norephedrine compared to the prior art best overall yield of 11%.

EXAMPLE 4

4-METHYL-5-PHENYL-3-OXAZOLIDINE PROPIONIC ACID METHYL ESTER (COMPOUND I)

200 ml of benzene, 43 g. (0.5 moles) of methyl acrylate and 76 g. of l-norephedrine are added to a 500 ml. three neck flask and refluxed overnight. To the solution is slowly added 15 g. (0.5 moles) of paraformaldehyde and the water removed using a Dean-Stark head. Concentrate the solution in vacuo on a steam bath and distill. The product boils at 137°–139° C./0.5 mm. The yield is 62 g.; $n^{24}d = 1.5155$.

EXAMPLE 5

1-(+)-α-[1-(3,3-di-3-THIENYL-2-PROPENYL) AMINO ETHYL] BENZENEMETHANOL HYDROCHLORIDE (COMPOUND III)

Add 82 g. (0.5 moles) of 3-bromothiophene in 300 ml. of anhydrous ether to a two liter three neck flask equipped with a stirrer, dropping funnel and dry ice condenser. Sweep the flask with nitrogen and with good stirring, drip in 32 g. (0.5 moles) of n-butyllithium (1.6 M in hexane) while keeping the reaction temperature at −60° to 70° C. with a dry ice/acetone bath. Stir an additional one half hour at −70° C. Add 62 g. (0.25 moles) of compound of Example 4 dissolved in 100 ml. of anhydrous ether keeping the temperature at −60° C. Stir one half at −70° C. and remove dry ice bath and allow to warm to 10° C. over two hours. Decompose by the slow addition of 500 ml. of water and separate the two layers. Wash the organic layer twice with 200 ml. of water and concentrate to an oil in vacuo on a steam bath. The intermediate oxazolidine is not isolated but is hydrolyzed to Compound III as in Example 3. The yield is 59%.

The foregoing examples and flow chart have been examplary of the invention only and not to be considered as placing any limitation on the invention. It is recognized that various departures may be made therefrom, which are within the scope of the accompanying claims, and do not depart from the principles of the invention.

What is claimed is:

1. Compounds of the formula

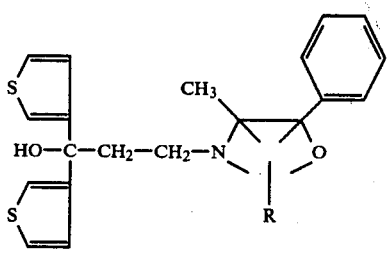
wherein R is hydrogen or lower alkyl.
2. Compound according to claim 1 wherein R is hydrogen.
3. Compound according to claim 1 wherein R is a straight chain lower alkyl.
4. Compound according to claim 1 wherein R is a branched chain lower alkyl.
5. α,α(di-3-thienyl)-4-methyl-5-phenyl-2-isopropyl-3-oxazolidine propanol.
6. α,α(di-3-thienyl)-4-methyl-5-phenyl-3-oxazolidine propanol.
* * * * *